United States Patent [19]
Benser

[11] Patent Number: 6,108,577
[45] Date of Patent: Aug. 22, 2000

[54] METHOD AND APPARATUS FOR DETECTING CHANGES IN ELECTROCARDIOGRAM SIGNALS

[75] Inventor: Michael Eric Benser, Birmingham, Ala.

[73] Assignee: Cardiac Pacemakers, Inc., St. Paul, Minn.

[21] Appl. No.: 09/299,507

[22] Filed: Apr. 26, 1999

[51] Int. Cl.[7] ................................................. A61B 5/0452
[52] U.S. Cl. ........................................... 600/517; 600/515
[58] Field of Search ..................... 600/509, 515, 600/517, 521

[56] References Cited

U.S. PATENT DOCUMENTS

| | | | |
|---|---|---|---|
| 4,546,776 | 10/1985 | Bellin et al. | 600/517 |
| 5,003,983 | 4/1991 | Dingwall et al. | 600/517 |
| 5,135,004 | 8/1992 | Adams et al. | 128/696 |
| 5,199,428 | 4/1993 | Obel et al. | 128/419 |
| 5,243,976 | 9/1993 | Ferek-Petric et al. | 607/6 |
| 5,316,001 | 5/1994 | Ferek-Petric et al. | 128/661.08 |
| 5,388,578 | 2/1995 | Yomtov et al. | 600/393 |
| 5,454,377 | 10/1995 | Dzwonczyk et al. | 128/734 |
| 5,497,780 | 3/1996 | Zehender | 128/696 |
| 5,522,854 | 6/1996 | Ideker et al. | 607/6 |
| 5,555,888 | 9/1996 | Brewer et al. | 128/702 |
| 5,694,943 | 12/1997 | Brewer et al. | 128/702 |
| 5,799,350 | 9/1998 | Ferek-Petric et al. | 607/17 |

OTHER PUBLICATIONS

Zehender, M., et al., "Continuous monitoring of acute mycoardial ischemia by the implantable cardioverter defribrillator.", *American Heart Journal*, vol. 127, No. 4, Part 2, 1057–1063, (Apr. 1994).

*Primary Examiner*—Kennedy Schaetzle
*Attorney, Agent, or Firm*—Schwegman, Lundberg, Woessner & Kluth, P.A.

[57] ABSTRACT

Method and apparatus for detecting changes in electrocardiogram signals. A first cardiac electrogram signal is sensed, where the first cardiac electrogram signal has a voltage and includes a first cardiac complex. A ventricular activation is detected in the first cardiac complex and a first timer is started, where the first timer times a first specified time. A first voltage value is measured from the first cardiac electrogram signal at the first specified time after the ventricular activation. A second voltage value is also measured from a defined portion of the first cardiac electrogram signal. A comparison value is then calculated from the first and second voltage values measured from the first cardiac electrogram signal. The first voltage value is recorded when the comparison value is greater than or equal to a predetermined value.

26 Claims, 5 Drawing Sheets

METHOD AND APPARATUS FOR DETECTING CHANGES IN ELECTROCARDIOGRAM SIGNALS

FIELD OF THE INVENTION

The present subject matter relates generally to medical devices and more particularly to a method and apparatus for detecting and recording changes in electrocardiogram signals.

BACKGROUND OF THE ART

Implantable cardiac rhythm management devices (ICRMDs) sense the heart's electrical activity and, if an arrhythmia is detected, deliver therapy to terminate it. Many patients with ICRMDs are at particular risk for myocardial ischemia, which has been reported to trigger arrhythmias (20–50% of ventricular tachyarrythmias).

Presently, to assess the presence or absence of ischemnia in patients, cardiac electrophysiologists (EPs) perform 12-lead body-surface electrocardiograms (ECGs) or 24-hour Holter monitoring. Myocardial ischemia has been known for years by EPs to be manifested on ECGs as ST-segment deviation (STD). Unfortunately, 12-lead ECGs are obtained over a short duration (<1 hour), and generally detect only chronic levels of ischemia. Holter recordings are more apt to detect transient ischemic events, but the 24-hour recording periods are still only snapshots of the patient's ischemic condition.

Recently, investigations have shown that similar STD changes occur in the electrograms from intra- and extracardiac signals. Other morphological features of electrocardiograms have also been reported to be representative of ischemia, including ST-segment-duration decrease, R-wave-duration increase, R-wave-amplitude decrease, T-wave duration/amplitude change, change in the rate of rise/fall of the T-wave, decrease in T-wave uniformity, and change in position of the J point.

Implantable medical devices have been suggested as being useful for signal analysis of the electrical potential curve sensed from the heart. One suggested approach has been to sense cardiac signals with an implantable medical device and then compare them to a template signal stored in the medical device. Based on this comparison, an assessment as to whether myocardial ischemia is present can be made. Using the stored template signal, however, may not yield the most accurate and reliable way of detecting the presence of myocardial ischemia. Once the template signal has been programmed, it remains constant. In contrast, the cardiac signals being sensed by an implantable device changes over time as a result of changes to the tissue that surrounds the implanted electrodes. As the tissues change, so do the signals the electrodes are able to sense. So, the cardiac signal sensed by the implantable medical device begins to change relative the stored template signal. As this change takes place, the template signal becomes less and less useful in identifying myocardial ischemia.

Additionally, the entire baseline value of the sensed cardiac signal may change over time. Gradual changes in the baseline value of a cardiac signal can indicate a change in cardiac condition which a physician may wish to investigate more closely. Thus, a need still exists for improvements in acquiring measurements and comparing those measurement in an effort to identify myocardial ischemia.

SUMMARY OF THE INVENTION

The present subject matter provides a method and an apparatus for detecting and recording myocardial ischemia. One unique aspect of the present subject matter is that the sensed electrocardiogram signal from which the assessment of myocardial ischemia is made is also used as the basis from which the comparison is made. So, the present system does not rely on a static template in order to identify the occurrence of myocardial ischemia in a sensed electrocardiogram signal.

According to the present subject matter, a first cardiac electrogram signal is sensed, where the first cardiac electrogram signal has a voltage and includes at least a first cardiac complex. As the first cardiac complex is sensed, a ventricular activation is detected in the first cardiac complex. A first voltage value is then measured from the first cardiac electrogram signal at a first specified time after the ventricular activation.

In addition to measuring the first voltage value, a second voltage value is also measured from the same first cardiac electrogram signal. The second voltage value is measured at a defined portion along the first cardiac electrogram signal. In one embodiment, the defined portion of the first cardiac electrogram signal is a portion within the first cardiac complex, Alternatively, the defined portion is in a second cardiac complex sensed in the first cardiac electrogram signal. A comparison value is then calculated from the first and second voltage values. The first voltage value is then recorded when the comparison value is greater than or equal to a predetermined value.

In one embodiment, the second voltage value is measured from a PQ or TQ segment of the first cardiac complex. The comparison value is calculated by subtracting the second voltage value from the first voltage value. This results in a voltage value which is then compared to a voltage value for the predetermined value.

Alternatively, a second cardiac complex is sensed in the first cardiac electrogram signal. The occurrence of the ventricular activation is detected in the second cardiac complex, and the second voltage value is measured at the first specified time after the ventricular activation. A voltage rate of change is then calculated for the comparison value from the first and second voltage values. The voltage rate of change is then compared to the predetermined value having the units volts/time.

In one embodiment, cardiac complexes in the cardiac electrogram signal are sensed and analyzed according to the present subject matter after a first predetermined time period. When a cardiac complex in the cardiac electrogram signal has a first voltage value, relative the second voltage value, that is greater than or equal to the predetermined value, then a second time period is used to analyze the sensed cardiac complexes. This second time period has a shorter interval than the first time period and overrides the use of the first time period. Cardiac signals are sensed and analyzed according to the present subject matter as the second time expires.

In one embodiment, when the comparison value for a cardiac complex is greater than or equal to the predetermined value the second time is restarted to allow for another cardiac complex to be analyzed after the second timer expires. Alternatively, when the comparison value for a cardiac complex is less than the predetermined value the second timer is stopped and the first timer is restarted to allow for another cardiac complex to be analyzed after the first timer expires.

DETAILED DESCRIPTION

In the following detailed description, reference is made to the accompanying drawings which form a part hereof and in which is shown by way of illustration specific embodiments in which the invention can be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

Figure 1:
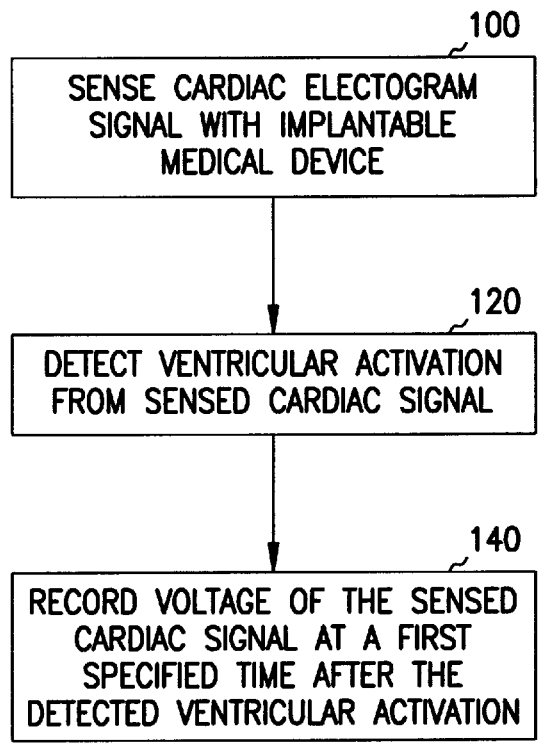
FIG. 1 is a flow chart illustrating one embodiment of the present subject matter.

Referring now to FIG. 1, there is shown a flowchart illustrating one embodiment of the present subject matter. At 100, at least a first cardiac electrogram signal is sensed by a diagnostic device, where the diagnostic device includes two or more electrodes for sensing cardiac electrogram signals. Moreover, the diagnostic device can either be an external or an internal device. An example of external devices include Holter monitors. An additional example includes an implantable cardiac rhythm management device (ICRMD), such as an implantable cardiac pacemaker or implantable cardioverter-defibrillator.

Two or more electrodes are used in conjunction with the diagnostic device to sense at least the first cardiac electrogram signal. In one embodiment, the first cardiac electrogram signal is sensed from a left ventricular location of a heart. Sensing electrogram signals from the left ventricular region of the heart is important as the left ventricle is responsible for pumping arterial blood and knowledge of ischemic events in this region can be used to provide better patient therapy.

In one embodiment, the first cardiac electrogram signal is a far-field electrogram signal, where the far-field signal has a voltage and includes cardiac complexes representative of at least a portion of the cardiac cycle. In an alternative embodiment, the first cardiac electrogram signal is a near-field electrogram signal, where the near-field signal also has a voltage and includes cardiac complexes representative of at least a portion of the cardiac cycle.

Electrogram signals can be sensed between any number of electrodes implanted or positioned in any number of locations in, on and around the heart. In one embodiment, the first cardiac electrogram signal is sensed between a first electrode positioned in the region of the left ventricle of a heart and a second electrode positioned away from the first electrode. For example, the first cardiac electrogram signal is sensed between a first electrode implanted within a coronary vein of the heart and the housing of the ICRMD. Alternatively, a second electrode, positioned outside the heart (e.g., positioned on the epicardial surface of the heart) is used in conjunction with the first electrode and the housing of the ICRMD to sense far-field signals across the left ventricular region of the heart.

In addition to sensing the first cardiac electrogram signal from the left ventricular region of the heart for use with the present subject matter, is it also possible to sense additional cardiac electrogram signals (e.g., a second cardiac electrogram signal, a third cardiac electrogram signal, etc.) between additional electrodes implanted in, on and around the heart. Therefore, additional electrocardiogram signals, including far-field and near-field cardiac signals, sensed across additional left ventricular locations and far-field and near-field cardiac signals, sensed across right ventricular locations, can be used with the present subject matter.

At 120, ventricular activation is detected from the first cardiac electrogram signal. In one embodiment, ventricular activation is detected when a predetermined portion of a QRS-complex is sensed in an electrogram signal. In one embodiment, the predetermined portion of the QRS-complex is a ventricular R-wave detected in the sensed cardiac complex. In one embodiment, the R-wave is identified by detecting a maximum deviation of the cardiac signal from a baseline signal during the QRS-complex. Other portions of the QRS-complex can also be detected to indicate ventricular activation, including the Q-wave (i.e., the start of the QRS-complex as noted by a sustained deflection from baseline signal). Additionally, different positions within a QRS-complex, including the R-wave, can be used to identify a ventricular activation.

A first voltage value is then measured from the first cardiac electrogram signal at a first specified time after the detection of the ventricular activation. The first specified time is a programmable value and can be selected to allow for a voltage measurement to be made at any portion along the cardiac signal. For example, a first specified time can be selected to allow for the cardiac signal voltage measurement, or measurements, to be made during the occurrence of an ST-segment of the cardiac cycle.

Figure 2:
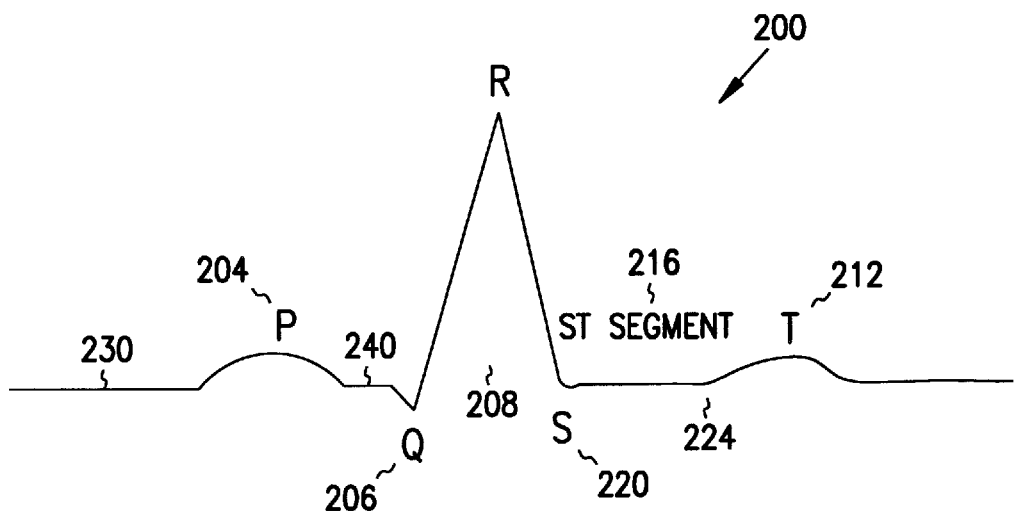
FIG. 2 is an electrocardiogram of a cardiac complex according to one embodiment of the present subject matter.

FIG. 2 shows one embodiment of a cardiac electrogram signal with a cardiac cycle 200. The cardiac cycle 200 is a composite electrogram signal sensed across a region of cardiac tissue. The cardiac cycle 200 includes a P-wave 204, representing a trial depolarization, a Q-wave 206, a QRS-complex 208, representing ventricular depolarization, and a T-wave 212, representing ventricular repolarization. An ST-segment 216 lies between the occurrence of the S-wave, approximately at 220, and the beginning of the T-wave 212, approximately at 224.

In one embodiment, measuring voltages of the cardiac signal during the ST-segment 216 is useful in detecting the presence of myocardial ischemia. When myocardial ischemia is present, the ST-segment 216 will deviate from a baseline value. In one embodiment, deviating from the baseline value can either be an ST-segment voltage value that is either elevated or depressed relative to the baseline value. In the example shown in FIG. 2, a baseline value is shown at 230 and has a value of approximately 0 volts. In an alternative embodiment, different portions of the cardiac electrogram signal can measured and used as baseline signals in the assessment of the ST-segment 216. For example, the voltage value of the electrogram signal in a PQ-segment 240 can be used to determine the change in ST-segment value for assessing the presence of myocardia ischemia. Additionally, the TQ-segment or the TP segment could also be used to determine the change in ST segment values.

In detecting a change in the ST-segment 216, a predetermined region of the ST-segment is defined from which to take a voltage measurement. In one embodiment, the predetermined region is taken as the voltage of the cardiac signal in the ST-segment at the first specified time after the ventricular activation. In one embodiment, the first specified time is selected in the range of 20 to 500 milliseconds, where 80 milliseconds is one of many appropriate values. In the present embodiment, however, it is understood that the first specified time will depend upon the portion of the cardiac complex that is taken to represent the ventricular activation, where an earlier portion of cardiac complex may require a longer first specified time as compared to a later portion of the cardiac complex which may require a shorter first specified time. The voltage of the cardiac signal sensed at the first specified time is then recorded at 140 and is retrievably stored for review and analysis.

Figure 3:
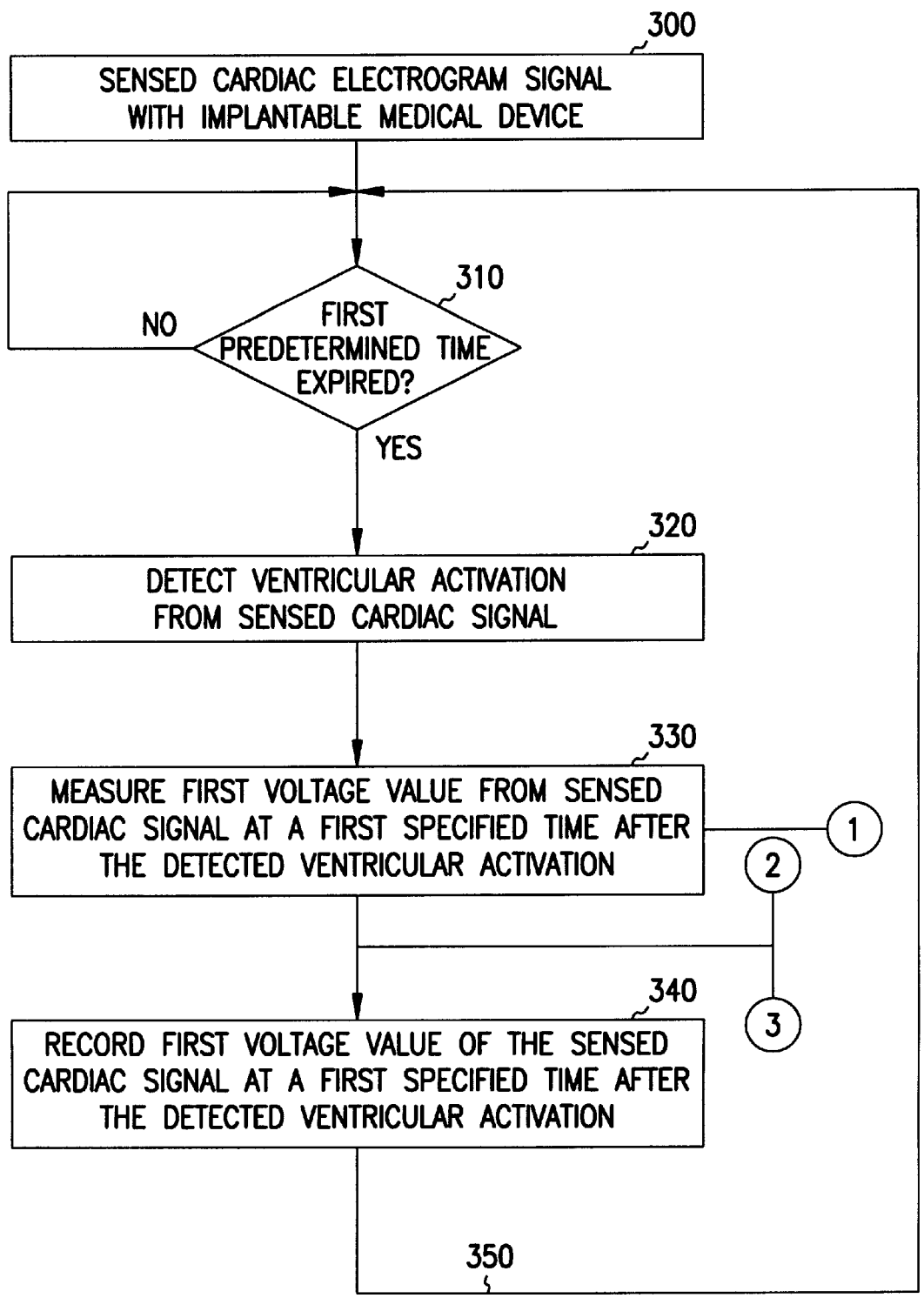
FIG. 3 is a flow chart illustrating one embodiment of the present subject matter.

Referring now to FIG. 3, there is shown an additional embodiment of the present subject matter. At 300, at least one cardiac electrogram signal is sensed by an ICRMD. In one embodiment, a first cardiac electrogram signal is sensed, where the signal has a voltage and includes at least a first cardiac complex. In addition to sensing cardiac electrogram signals, a first timer is also started. The first timer counts off a first predetermined time, after which voltage values are measured from the cardiac electrogram signals. In one embodiment, the first predetermined time is an interval over which the ICRMD waits, or delays, before measuring and analyzing the cardiac electrogram signals.

At 310, the first predetermined time is analyzed to determine whether the first time has expired. When the first time has not expired, a path is taken back to 310 to make another inquire whether the first predetermined time has expired. In one embodiment, the first predetermined time is a programmable time period of between 1 second and 7 days. Alternatively, the programmable time period is between 1 minute and 24 hours. In one embodiment, a first time period of 5 minutes is an acceptable value.

When the predetermined time expires, a path is taken to 320. At 320, a ventricular activation is detected in the first cardiac complex in the first cardiac electrogram signal. In one embodiment, ventricular activation is detected from a far-field signal as previously described. In an alternative embodiment, a near-field electrogram signal sensed across a ventricular location is used to detect the occurrence of a ventricular activation. The near-field electrogram signal can detect the occurrence of ventricular R-waves, which are used to indicate the occurrence of ventricular activation. For example, determining the occurrence of ventricular activation from the near-field signal can include determining a maximum deflection point of the near-field electrogram signal sensed for the cardiac complex. The maximum deflection point of the near-field signal is then taken as the occurrence of the ventricular activation. Alternatively, the start (or beginning) of the deflection in the cardiac signal indicating ventricular activation is used as the occurrence of ventricular activation. Other portions of the near-field signal could also be taken as indicating ventricular activation, where one factor in determining an appropriate choice would be the repeatable nature of the portion of the near-field signal.

In one embodiment, a near-field electrogram signal is sensed from a right ventricular region of the heart between a pacing/sensing electrode and an additional electrode. For example, sensing the near-field electrogram signal can include sensing the signal between a pacing/sensing electrode and a defibrillation coil electrode both positioned along a transvenous catheter. Alternatively, the near-field signal is sensed between the pacing/sensing electrode and the housing of the ICRMD.

Once the ventricular activation is sensed, at 330 a first voltage value of the first cardiac electrogram signal is measured at a first specified time after the ventricular activation determined from the first cardiac complex. In one embodiment, the first specified time is determined by the attending physician. The first specified time after the ventricular activation is a predetermined value in the range of between 20 to 500 milliseconds, where 80 milliseconds is an appropriate value.

In an alternative embodiment, the value of the first specified time depends on the sensed ventricular activation rate. One aspect of the present subject matter is to make voltage measurements along cardiac signals within a particular portion of the cardiac cycle. For example, voltage measurements taken from cardiac signals along the ST-segment of a cardiac complex are useful in determining the occurrence of myocardial ischemia as previously discussed. As the ventricular rate increases, the time in which the cycle occurs decreases. This decrease in the cycle results in a decrease in the relative time between the portions of the QRS-complex and the ST-segment (e.g., the time between the R-wave and T-wave begins to decrease as the heart rate increases). Thus, as the ventricular rate changes, so does the location of the ST-segment relative the ventricular activation.

In the present embodiment, the first specified time is calculated by taking a percentage of the time of a ventricular interval. In one embodiment, the ventricular interval is calculated from consecutively sensed ventricular activations. For example, a second cardiac complex is sensed in the first cardiac signal, where the second cardiac complex precedes the first cardiac complex. From these two cardiac complexes a ventricular activation interval is calculated. The first specified time is then calculated by taking a first predetermined percentage of the ventricular activation interval. So, as each ventricular activation interval is calculated, the first specified time is calculated by multiplying the time of the ventricular interval by the first predetermined percentage. In one embodiment, the first predetermined percentage is a programmable value in the range of approximately 2 to 50 percent of the ventricular activation interval. Alternatively, the range is approximately 10 to 20 percent of the ventricular activation interval.

In an additional embodiment, when two consecutive ventricular activations are sensed, the rate of ventricular activations will be assessed only on ventricular activations that are, in the case of patients in sinus rhythm, beats originating from the atrium (atrially paced or sinus beats). In the case of patients being paced in the ventricle, the implantable pulse generator would have the programmed rate. Furthermore, in the case of a patient in an atrial tachyarrhythmia, the entire basing of the ST (and PQ or TQ) regions on the ventricular rate would not be valid. In one embodiment, the mechanisms by which beats are analyzable or not could be based on the morphology of the R wave or, more simply, by the consistency of the rate (or rather, the lack of a high standard deviation of RR intervals).

In an alternative embodiment, the first voltage value is calculated from two or more voltage values measured, or acquired, from the first cardiac electrogram signal. For example, two or more voltage values measured from a far-field electrogram signal are used to calculate the first voltage value. One way of acquiring these two or more voltage values is to make voltage measurements at a predetermined sampling frequency in the interval between the first specified time and a second specified time after the occurrence of the ventricular activation. In one embodiment, the second specified time is timed by the voltage acquisition timer. In one embodiment, the sampling frequency is a programmed value in the range of between 10 Hz and 10 kdHz, where 100 Hz is an appropriate value. The second specified time is also a programmable value, where the second specified time is programed in the range of between 5 milliseconds to 600 milliseconds.

Alternatively, the second specified time is calculated by multiplying the ventricular activation interval (as previously described) by a second predetermined percentage. In one embodiment, the second predetermined percentage has a value greater than the first predetermined percentage used to calculate the first specified time such that two or more voltage measurements can be made in the interval between the first and second specified times. In one embodiment, the second predetermined percentage is a programmable value in the range of 2 percent to 50 percent of the ventricular activation interval.

Once the multiple voltage measurements have been acquired for each sensed electrogram, the first voltage value is calculated from the two or more voltage values measured during interval between the first and second specified time for each sensed electrogram. In one embodiment, the first voltage value for each sensed electrogram is an average voltage value of the voltage values measured during the interval. Alternatively, the first voltage value for each sensed electrogram is a median voltage value of the voltage values measured during the interval.

The voltage of the cardiac signal is then recorded at 340 and path 350 is taken back to 300 where the first timer begins to time the first predetermined time again. In addition to recording the voltage of the cardiac electrogram signal, the time at which the cardiac complex occurred is also recorded. Additional information related to the cardiac state can also be recorded and stored for retrieval and/or analysis at a later time. Such information can include, but is not limited to, ST slope, R wave amplitude and duration, PR interval, T wave duration, and T wave amplitude.

Figure 4:
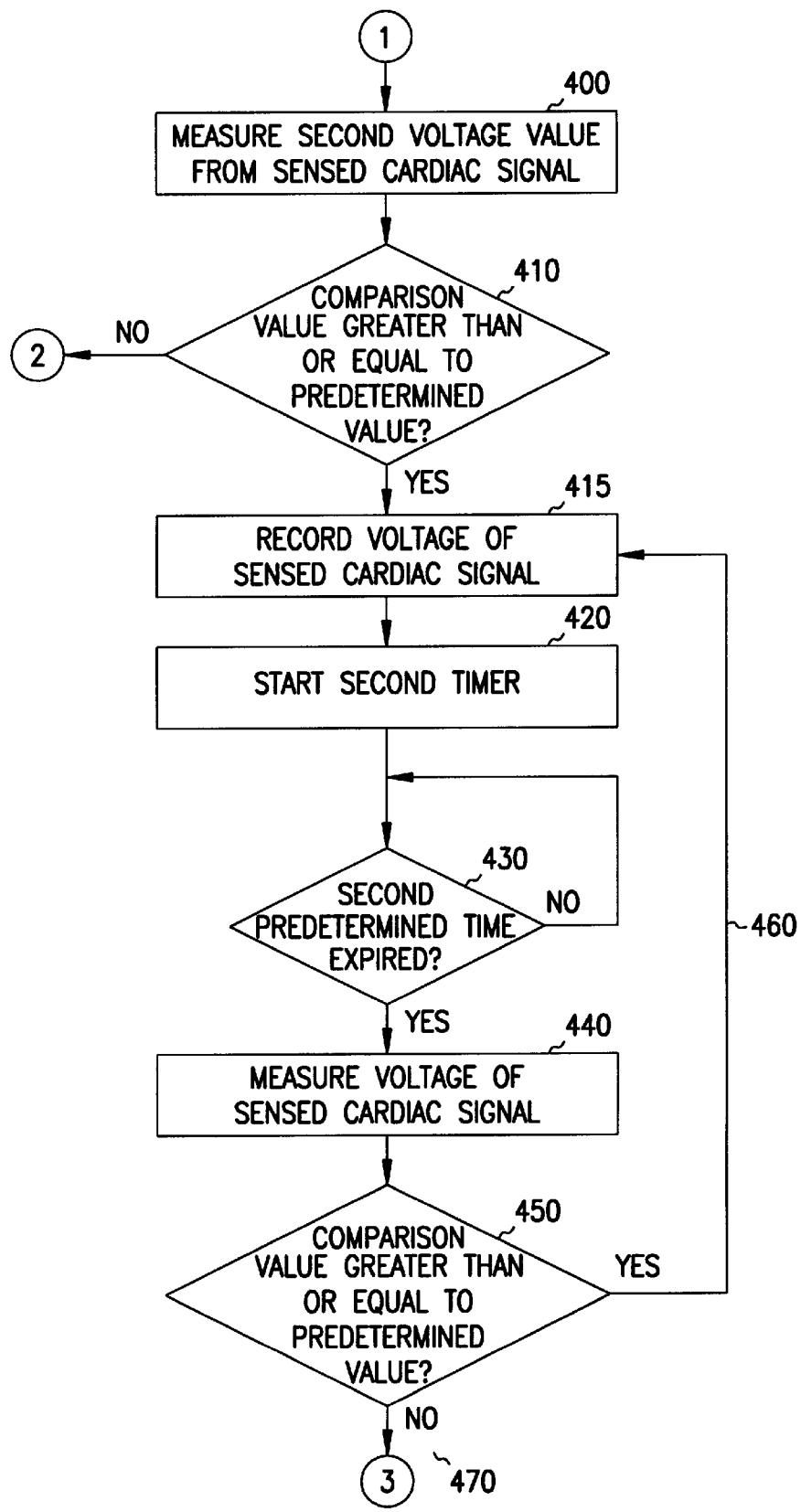
FIG. 4 is a flow chart illustrating one embodiment of the present subject matter.

Referring now to FIG. 4, there is shown an additional embodiment of the present subject matter. In FIG. 4, an encircled number one connects to the encircled number 1 shown in FIG. 3. After measuring the cardiac signal voltage at 330, a path, connected by the encircled number ones, is taken to 400. At 400, a second voltage value is measured at a defined portion of the first cardiac electrogram signal. In one embodiment, the second voltage value is measured from at least one point between the P-wave and the Q-wave of the first cardiac complex. In one embodiment, this value is measured at a predetermined time after the occurrence of the P-wave, but before the beginning of the Q-wave. In an alternative embodiment, the second voltage value could be measured in a region between the T-wave and the Q-wave of the first cardiac complex. Selection of either the PQ-region of the TQ-region will be dependent upon where, and how many, electrodes are positioned in order to sense the cardiac signal. In an additional embodiment, is it possible to take multiple measurements along these regions and determine the value by taking the average or median value.

The first voltage value and the second voltage value measured from the first cardiac complex are then used to calculate a comparison value. In one embodiment, the comparison value is calculated by subtracting the second voltage value from the first voltage value. An absolute value of the difference is then taken, and the comparison value is subsequently compared to a predetermined value. In one embodiment, the predetermined value is a programmable value between approximately 0.01 and 10 millivolts. In an alternative embodiment, the predetermined value is a programmable value between approximately 0.2 and 0.4 millivolts.

In an alternative embodiment, a rate of voltage change is calculated between the first and second voltage values. For example, a second cardiac complex is sensed in the first cardiac electrogram signal. In one embodiment, the second cardiac complex precedes the first cardiac complex. The occurrence of the ventricular activation is determined from the second cardiac complex, as previously described. The second voltage value is then measured from the cardiac signal at the first specified time after the ventricular activation determined from the second cardiac complex. The comparison value is then calculated from the first and second voltage values by calculating a rate of voltage change between the first and second voltage values. The comparison value is then compared to the predetermined value. In the present embodiment, the predetermined value is a rate of change threshold value. In one embodiment, the rate of change threshold value is a programmable value in the range of 0.001 to 50 millivolts/minute.

At 410, the comparison values compared to the predetermined value to determine whether the comparison value is greater than or equal to the predetermined value. When the comparison value is less than the predetermined value, the path is taken, via the encircled two, from 410 to 340 on FIG. 3 where the first voltage value is recorded. Alternatively, when the comparison value is greater than or equal to the predetermined value, the path is taken to 415. At 415, the first voltage is recorded. In addition to recording the first voltage, additional information related the first cardiac complex, and the second cardiac complex, are recorded. As previously discussed, information related to the cardiac complex can include the voltage of the cardiac signal at the first specified time, the time the cardiac complex occurred, the heart rate, raw electrocardiogram signals, and other cardiac information as is known.

In addition to recording the voltage of the sensed cardiac signal at the first specified time, a second timer is started at 420. The second timer times out a second predetermined time and overrides the first timer. In one embodiment, the second predetermined time is of a shorter duration than the first predetermined time period used at 310. This allows for cardiac complexes to be analyzed and recorded at a more rapid rate once the first cardiac complex is detected as having a first voltage value that exceeds the first predetermined value as previously described. In one embodiment, the second predetermined time is a programmable value in the range of 0.5 seconds to one hour, where 30 seconds is an appropriate value.

At 430, the second predetermined time is examined to determine if it has expired. When the time has not expired, a path is taken back to 430 to inquire again if the time has expired. When the time expires, a path is taken to 440. At 440, the first voltage value and the second voltage value from the electrogram signal are measured as previously described. The comparison value is then calculated and compared to the predetermined value at 450 as previously described. When the comparison value is greater than or equal to the predetermined value, path 460 is taken back to 410 where the first voltage value of the sensed cardiac signal is recorded in a manner previously described. The second predetermined time is then restarted at 420 to allow for additional cardiac complexes to be sensed and analyzed.

Alternatively, when the comparison value is less than the predetermined value, path 470 is take to encircled number 3.

Encircled number 3 connects to 340 in FIG. 3. At 340, the first voltage value is then recorded as previously described.

After recording the first voltage value at 340, the first predetermined time is started and tested at 310 as previously described.

In an alternative embodiment, at 450 the comparison value is the rate of voltage change between a first voltage value for a first cardiac complex and a second voltage value for a second cardiac complex is used to determine whether to return to 415 or to take path 470 to 340. In the present embodiment, assume a first voltage value has been recorded at 410 after it is determined the comparison value is greater than or equal to the predetermined value. After the second predetermined time expires, the second voltage value is measured from the second cardiac complex at 440. At 450, the rate of voltage change is then calculated for the first and second voltage values. The rate of voltage change (i.e., the comparison value) is then compared to the predetermined value to determine whether to proceed back to 415 or to340. When returning to 415, the rate of voltage change calculated at 450 will be determined from the second voltage value (measured after the second predetermined time) and the subsequent voltage value (e.g., a third voltage value measured from a third cardiac complex) measured from a cardiac complex sensed after the second predetermined time. In one embodiment, the rate of change threshold (the predetermined value) is a programmable value in the range of between 0.10 and 1.0 millivolts/minute.

In an additional embodiment, a rate of voltage change is calculated between a comparison value calculated for the first cardiac complex and a comparison value calculated for a second cardiac complex sensed in the first cardiac signal. For example, the second cardiac complex is sensed in the first cardiac electrogram signal, and the occurrence of the ventricular activation from the second cardiac complex is detected. The first voltage value of the first cardiac electrogram signal is then measured at the first specified time after the ventricular activation determined from the second cardiac complex. The second voltage value is measured at the defined portion of the first cardiac electrogram signal from the first cardiac complex. The second voltage value is also measured at the defined portion of the first cardiac electrogram signal from the second cardiac complex, where the second voltage value measured for the first cardiac complex is a separate second voltage value than the second value measured for the second cardiac complex. A comparison value is then calculated for the first cardiac complex from the first and second voltage values measured from the first cardiac complex. Likewise, a comparison value is calculated for the second cardiac complex from the first and second voltage values measured from the second cardiac complex. A rate of voltage change is then calculated from the comparison value for the first cardiac complex and the comparison value for the second cardiac complex. The rate of voltage change is then compared to the predetermined value (in millivolts/minute) and the first voltage value of both the first cardiac complex and the second cardiac complex are recorded when the rate of voltage change is greater than or equal to the predetermined value. Additionally, the present embodiment can be used to assess which path to take after 410 and/or 450.

In an additional embodiment, additional algorithms for determining when to proceed from using the first timer to using the second timer (i.e., moving from 400 to 420 and from 450 to 410 via path 460) are also within the scope of the present subject matter. For example, additional algorithms can be based on best-fitting trended (past) values of the difference between voltage values from ST segments and TQ or PQ segments over certain durations. The determination to begin the second timer would then be based on parameters from these best fits (linear or higher order fits). Alternatively, a threshold could alternatively be set based on the natural variation of the relevant parameter. So, for example, if a patient has a period of ST segment levels in which the standard deviation of all of the values are, for example, 0.02 mV, then the threshold for beginning the second timer would be a value proportional to this standard deviation. And if a patient has highly fluctuating ST levels, this patient may have a proportionately higher threshold for starting the second timer.

In an additional embodiment, once 415 is reached a duration timer is started. In one embodiment, the duration timer times an interval over which the second time period overrides the first time period. In other words, the duration timer times an interval over which the path is taken from 450 to 415, regardless of the result at 450, during the interval. Thus, when 410 is satisfied (i.e., the path is taken to 415) the duration timer is started. Running concurrently with the duration timer is the second timer. The second timer times out the second predetermined time after which the voltage values are measured from the cardiac signals at 440. At 450, the duration timer is checked to see if it has expired. When the duration timer has not expired, path 460 is taken to 415 where the voltage value is recorded and the second timer is started again at 420. When the duration timer expires, the comparison value is compared to the predetermined value at 450 as previously described. The path taken from 450 then depends upon the result of the comparison at 450. In one embodiment, the interval of the duration timer is a programmable value in the range of 1 to 60 minutes, where 10 minutes is an acceptable value.

Electrodes for sensing cardiac signals can be placed at any number of positions within and outside of the heart. For example, electrodes can be placed in the left ventricular region of the heart for sensing cardiac signals. In one embodiment, a transvenous lead (or catheter) having at least a first electrode positioned along the peripheral surface of the catheter is positioned within the coronary vein, with the second electrode positioned in the thoracic cavity. In one embodiment, the first electrode is positioned in the coronary sinus. In an alternative embodiment, the first electrode is positioned within a coronary vein and extending toward the heart's apex along one of the primary branches from the coronary sinus, such as the anterior interventricular branch, a lateral branch, or the posterior interventricular branch to position the first electrode adjacent the left ventricle. In one embodiment, the first at least one coil electrode is situated near the catheter's distal end, such that it resides along the ventricular epicardium, and not along the atrioventricular groove.

Alternatively, the first and/or second electrodes are positioned in an intrathoracic space. In an alternative embodiment, the first electrode is positioned in the intrapericardial space, including directly on the epicardium, which involves accessing the pericardial space through the pericardium sack. The electrode is then positioned within the intrapericardial region between the pericardium sack and the epicardial surface of the heart. The electrode is then used to sense the first cardiac signal between a second electrode positioned in a thoracic cavity. Alternatively, the first cardiac signal can be sensed between the first electrode and one or more other implanted electrodes.

In addition to sensing cardiac complexes from the left ventricular locations, additional cardiac complexes can be sensed from other location within and on the heart. For example, cardiac signals can be sensed from the right ventricular region along with the sensed cardiac signals from the left ventricular region. In one embodiment, sensing a cardiac signal, or signals, from the right ventricular region is accomplished through the use of an Endotak transvenous electrode catheter (CPI/Guidant, St. Paul, Minn.). The Endotak catheter includes a sensing/pacing tip electrode for sensing near-field ventricular signals, and a first and second defibrillation coil electrode used in sensing far-field cardiac signals. Cardiac signals sensed from both the right and left ventricular regions can then be analyzed as previously described. In one embodiment, sensing and analyzing both far-field signals allows the ischemic state of the heart to be more accurately assessed than the situation where only the far field signal sensed from the right side of the heart is analyzed.

Figure 5:
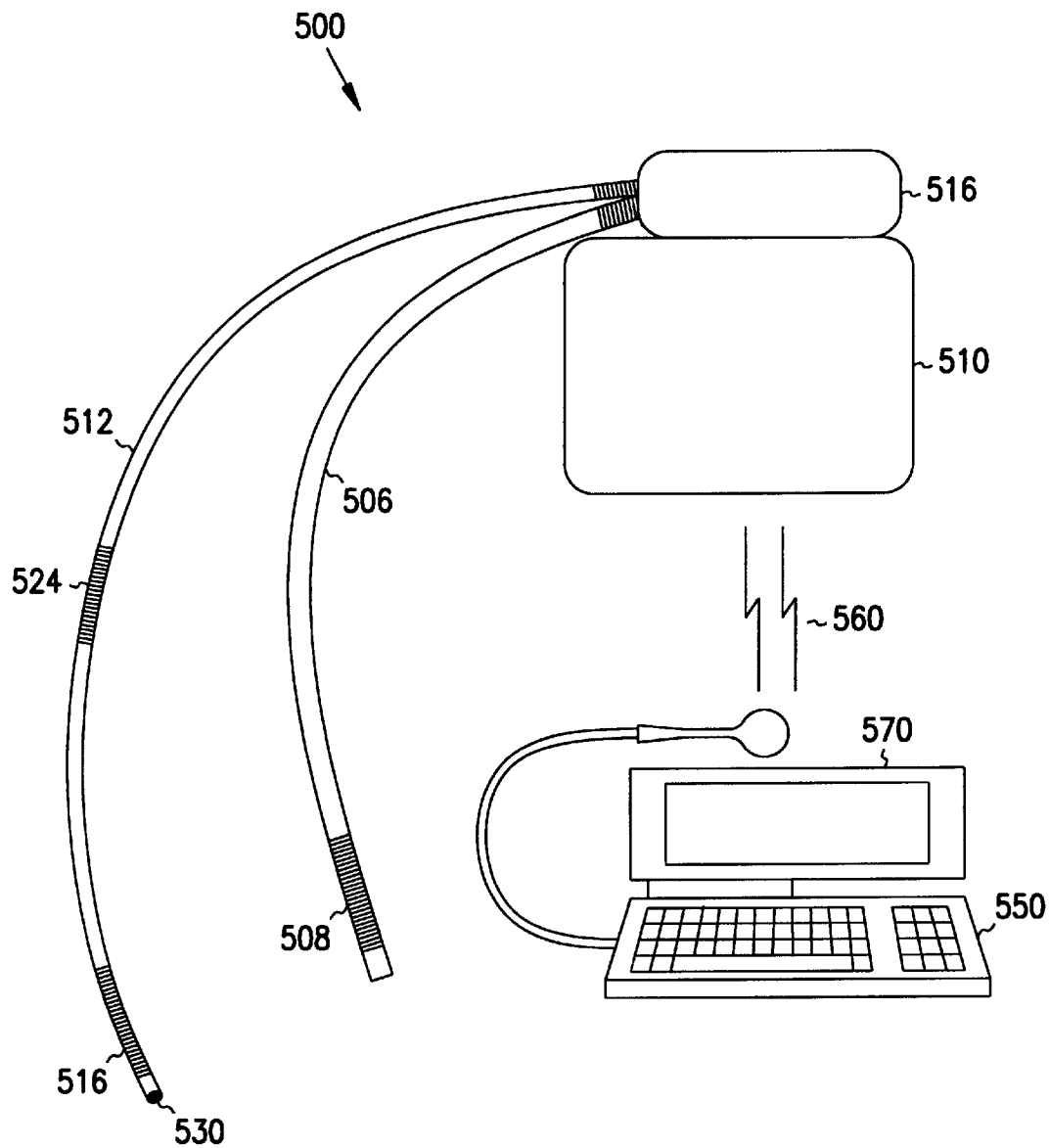
FIG. 5 is a schematic of a system according to one embodiment of the present subject matter.

Referring now to FIG. 5, there is shown one embodiment of a system 500 according to the present subject matter. The system 500 includes a first catheter 506 physically and electrically coupled to an implantable cardiac rhythm management device (ICRMD) 516. Examples of ICRMDs 516 include implantable cardioverter defibrillators (ICDs), ICDs with cardiac pacing capabilities, and implantable cardiac pacemakers.

In one embodiment, the first catheter 506 includes a first electrode 508 positioned along the peripheral surface of the first catheter 506. In one embodiment, the first electrode 508 is positioned adjacent the distal end of the first catheter 506. In an additional embodiment, the housing of the ICRMD 516 is a second electrode 510 and is used to sense far-field signals between the first electrode 508 and the second electrode 510.

In addition to having the first catheter 506, it is possible to have additional catheters physically and electrically coupled to the ICRMD. For example, a second catheter 512 can be included in the present system, where the second catheter 512 includes a third electrode 516, a fourth electrode 524 and a sensing/pacing electrode 530. The electrodes 516, 524 and 530 are positioned on the peripheral surface of the second catheter 512 and electrically coupled to electronic control circuitry contained within the ICRMD 516. In one embodiment, the second catheter 512 is an Endotak lead™ (CPI/Guidant, St. Paul, Minn).

The ICRMD 516 contains control circuitry which receives cardiac signals sensed between predetermined combinations of electrodes and the housing of the ICRMD 516. The control circuitry housed within the ICRMD 516 amplifies the cardiac signals being sensed between the electrodes and the housing and analyzes and records cardiac data on a plurality of cardiac complexes as previously described.

In addition to measuring and recording the cardiac signals during the cardiac complexes, the ICRMD 516 includes telemetry circuitry which allow for communication with a medical device programmer 550. In one embodiment, medical device programmer 550 is used to receive and transmit programming and operating instructions, including those for carrying out the present subject matter, to the ICRMD 516. Additionally, the medical device programmer 550 is used to download data relating to the recorded voltages and cardiac complexes analyzed using the control circuitry housed within the ICRMD 516. In one embodiment, the commands, instructions and data are transmitted over a radio frequency telemetric link 560 established between the ICRMD 516 and the medical device programmer 550.

Upon downloading data relating to the plurality of cardiac complexes, the medical device programmer 550 may be used to plot the voltage values recorded for the plurality of cardiac complexes as a function of time when the cardiac complex occurred. In one embodiment, this information is plotted on a display screen 570 of the medical device programmer 550 for review and analysis. This information can then be used in identifying the occurrence of myocardial ischemia. For example, upon plotting the voltage levels of the cardiac complexes as a function of time, regions along the plot where the values of voltages deviate from approximately zero (little to no deviation from the first standard) can be located and identified as regions indicating the occurrence of an ischemic event. In addition, knowledge of the ischemic history of a patient could be useful in selecting/optimizing device-based therapy for the prevention of arrhythmia onset. Additional information related to each of the plotted points can also be recalled and displayed on the display screen 570 by using a pointing device, such as a computer mouse, to highlight and select a cardiac complex of interest.

Figure 6:
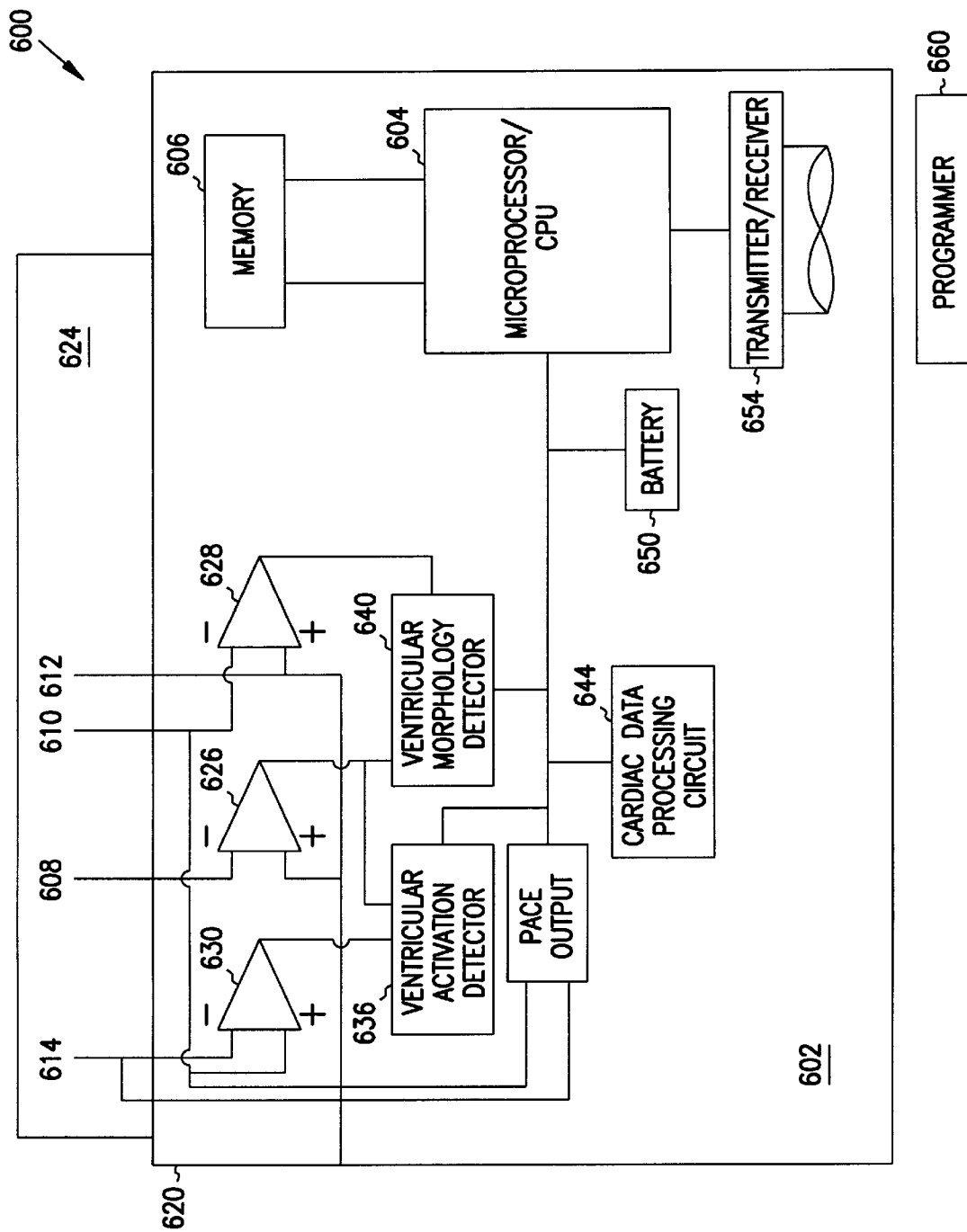
FIG. 6 is a block diagram of an implantable medical device according to one embodiment of the present subject matter.

Referring now to FIG. 6, there is shown an embodiment of a block diagram of an implantable cardiac rhythm management device (ICRMD) 600. The ICRMD 600 includes control circuitry 602 which receives one or more cardiac signals and determines and records the voltage of the cardiac signals during predetermined portions of sensed cardiac complexes. In one embodiment, the control circuitry 602 is a programmable microprocessor-based system, with a microprocessor 604 and a memory circuit 606, which contains parameters for various pacing and sensing modes and stores data indicative of cardiac signals received by the control circuitry 602. The control circuitry 602 further includes terminals labeled with reference numbers 608, 610, 612 and 614 for connection to the electrodes attached to the surface of a first catheter and a second catheter as previously described.

The control circuitry 602 is encased and hermetically sealed in a housing 620. In one embodiment, the housing 620 is suitable for implanting in a human body. In one embodiment, the housing 620 is made of titanium, however, other biocompatible housing materials as are known. A connector block 624 is additionally attached to the housing 620 to allow for the physical and the electrical attachment of catheters and electrodes to the ICRMD 600 and the encased control circuitry 602. In one embodiment, the connector block 624 includes at least a first input/output socket (not shown) for allowing a lead connector of the first catheter to be coupled to the ICRMD 600. In the present embodiment, a first and second input/output sockets are provided to allow for the lead connectors of the first and second catheters to be coupled to the ICRMD 600.

The ICRMD 600 includes terminal 608 which receives electrical signals from the first electrode 508. Terminal 608 and the housing 620 are coupled to sense amplifier 626 to allow for a first cardiac signal (a far-field signal) to be sensed between the first electrode 508 and the housing 620. The ICRMD 600 also includes terminals 610 and 612 which are coupled to the third electrode 516 and the fourth electrode 524, respectively. In addition, the housing 620 of the ICRMD 600 is coupled in common with the fourth electrode 524. Terminals 610 and 612 are coupled to sense amplifier 628 to allow for a second cardiac signal (a far-field signal) to be sensed between the third electrode 516 and the fourth electrode 524. Alternatively, the second cardiac signal is sensed between the third electrode 516 and the fourth electrode 524/housing 620, which are in common. The ICRMD 600 further includes terminal 614 which receives electrical signals from the pacing/sensing electrode 530. The terminals 610 and 614 are coupled to sense amplifier 630 to allow for a third cardiac signal (a near-field signal) to be sensed between the pacing/sensing electrode 530 and the third electrode 516. Other catheter and electrode combinations can also be used with the present embodiment. Additionally, changes to the number and types of catheters, electrodes and sensing electronics can be made to the present system without departing from the present subject matter.

The ventricular activation detector circuit 636 is coupled to the first input/output socket, where the ventricular activation detector circuit receives a first cardiac signal through the first input/output socket and analyzes the first cardiac signal to detect the occurrence of a ventricular activation in a first cardiac complex. In one embodiment, the first cardiac signal is received from sense amplifier 630, which is coupled to the ventricular activation detector 636. In one embodiment, the first cardiac signal is a near-field signal which the ventricular activation detector circuit 636 analyzes to detect the occurrence of ventricular activations.

Alternatively, the first cardiac signal is received from sense amplifier 626, which is coupled to the ventricular activation detector 636. In one embodiment, the first cardiac signal is a far-field signal sensed between the first electrode and the housing 620 for which the ventricular activation detector circuit 636 analyzes to detect the occurrence of ventricular activations.

The cardiac morphology detector circuit 640 is also coupled to the first input/output socket. In one embodiment, the output of sense amplifiers 626 and 628 are shown coupled to cardiac morphology detector 640 so that the cardiac morphology detector circuit 640 receives the first cardiac signal through the first input/output socket. The cardiac morphology detector circuit 640 is also coupled to the ventricular activation detector circuit 636. The cardiac morphology detector circuit 640 analyzes the first cardiac signal to detect the occurrence of cardiac complexes.

As a cardiac complex is sensed by both the ventricular activation detector circuit 636 and the cardiac morphology detector circuit 640, the ventricular activation detector 636 detects the occurrence of the ventricular activation and provides a signal to the cardiac morphology detector circuit 640. When the cardiac morphology detector circuit 640 receives the signal, it measures the first voltage value from the cardiac signal at the first specified time after the ventricular activation in the cardiac complex. In one embodiment, the first specified time after the ventricular activation is a programmable value which is stored in the memory 606 of the ICRMD 600.

In an additional embodiment, the cardiac morphology detector circuit 640 measures two or more voltages of the first cardiac electrogram signal at a predetermined sampling frequency between the first specified time and a second specified time after the occurrence of the ventricular activation. The cardiac morphology detector circuit 640 then calculates the first voltage value of the first cardiac electrogram signal from the two or more voltages as previously described. In one embodiment, the predetermined sampling frequency is programmed into the ICRMD 600 and used by the cardiac morphology detector 640 to time the voltage measurements.

In an alternative embodiment, the first specified time is calculated from consecutively sensed pairs of ventricular activations (ventricular intervals) sensed from cardiac complexes. For example, the ventricular activation detector circuit 636 analyzes the first cardiac signal to detect the occurrence of ventricular activation in a second cardiac complex, wherein the second cardiac complex precedes the first cardiac complex. The cardiac morphology detector circuit 640 then calculates a ventricular activation interval from the ventricular activation of the first cardiac complex and the ventricular activation of the second cardiac complex. The cardiac morphology detector circuit 640 then calculates the first specified time by taking a predetermined percentage of the ventricular activation interval as previously discussed.

The cardiac morphology detector circuit 640 also measures the second voltage value of the first cardiac electrogram signal at the defined portion of the first cardiac complex as previously discussed. In one embodiment, the cardiac morphology detector circuit 640 measures the second voltage value between the P-wave and the Q-wave of the first cardiac complex. A cardiac data processing circuit 644 is also included in the control circuitry 602, and is coupled to the ventricular activation detector circuit 636 and the cardiac morphology detector circuit 640. The cardiac data processing circuit 644 calculates the comparison value from the first and second voltage values.

The microcontroller 604 is coupled to the cardiac data processing circuit 644 the ventricular activation detector circuit 636 and the cardiac morphology detector circuit 640. The microcontroller 604 receives the comparison value from the cardiac data processing circuit 644. The microcontroller 644 then compares the comparison value to the predetermined values stored in the memory 606 to determine whether the comparison value is greater than or equal to the predetermined value. The microprocessor 604 then records the first voltage value in the memory 606 when the comparison value is greater than or equal to a predetermined value.

As previously discussed, a first timer is used to time a first predetermined time over which the ICRMD 600 waits before carrying out the described subject matter. The microcontroller 640 contains the first timer which counts off the first predetermined time. When the first time expires the microcontroller 640 controls the ventricular activation detector circuit 636 and the cardiac morphology detector circuit 640 to analyze the cardiac signals, such as the first cardiac signal, to detect the occurrence of the ventricular activation in the first cardiac complex, and to preform the previously described operations.

In an additional embodiment, the microcontroller 605 contains the second timer. The second timer overrides the first timer and counts off the second predetermined time, which is shorter in duration than the first predetermined time. The microcontroller 604 starts the second timer when the comparison value is greater than or equal to the predetermined value. After the second time expires, the microcontroller 604 signals the ventricular activation detector circuit 636 and the cardiac morphology detector circuit 640 to analyze the first cardiac signal for the occurrence of the ventricular activation in the first cardiac complex and to measure the first and second voltage values after the second predetermined time expires. The microprocessor 604 then restarts the second timer when the comparison value is greater than or equal to the predetermined value. The second predetermined time is a programmable value which is stored in the memory 606 of the ICRMD 600.

In addition to the second timer, the microcontroller 604 can also contain a duration timer which counts off a duration interval time. In one embodiment, the microcontroller 604 starts the duration timer and the second timer when the comparison value is greater than or equal to the predetermined value. The microcontroller 604 then signals the ventricular activation detector circuit 636 and the cardiac morphology detector circuit 640 to analyze the first cardiac signal for the occurrence of the ventricular activation in the first cardiac complex after the second predetermined time expires. The cardiac morphology detector circuit 640 then measures the first and second voltage values. The microprocessor 604 then restarts the second timer again, and continues to use the second timer while the interval of the duration timer is being timed.

As previously discussed, the rate of voltage change between portions of cardiac complexes can be used to determine whether to begin measuring voltage values at the second predetermined time period. In one embodiment, the ventricular activation detector circuit 636 analyzes the first cardiac signal for the occurrence of ventricular activation in a second cardiac complex. The cardiac morphology detector circuit 640 also analyzes the first cardiac signal for the occurrence of the second cardiac complex. The cardiac morphology detector circuit 640 then measures the second voltage value from the first cardiac signal at the first specified time after the ventricular activation in the second cardiac complex. The cardiac data processing circuit 644 then calculates the comparison value as a rate of voltage change between the first and second voltage values. Additionally, the cardiac data processing circuit 644 can be used to calculate the rate at which voltage values change between consecutively measured cardiac complexes once the use of the second specified time period has begun.

In an additional embodiment, the ventricular activation detector circuit 636 analyzes the first cardiac signal for the occurrence of ventricular activation in a second cardiac complex. In addition to the ventricular activation detector circuit 636 sensing the second cardiac complex, the cardiac morphology detector circuit 640 also senses and analyzes the second cardiac complex in the first cardiac signal. The cardiac morphology detector circuit 640 then measures the first voltage value of the first cardiac signal at the first specified time after the ventricular activation in the second cardiac complex. In addition, the cardiac morphology detector circuit 640 measures the second voltage value at the defined portion of the first cardiac signal from the first cardiac complex. Also, the cardiac morphology detector circuit 640 measures the second voltage value at the defined portion of the first cardiac signal from the second cardiac complex.

As each of the first and second voltage values are measured from the first and the second cardiac complexes, then are supplied to the cardiac data processing circuit 644. As the first and second voltage values measured from the first cardiac complex are measured, the cardiac data processing circuit 644 calculates the comparison value. Likewise, as the first and second voltage values are measured from the second cardiac complex, the cardiac data processing circuit 644 calculates the comparison value for the second cardiac complex. The cardiac data processing circuit 644 then calculates the rate of voltage change between the comparison value calculated from the first cardiac complex and the comparison value calculated from the second cardiac complex. The microcontroller 604 then records the first voltage value of both the first cardiac complex and the second cardiac complex in the memory 606 when the rate of voltage change is greater than or equal to the predetermined value.

Power for the ICRMD 600 is supplied by battery 650. In addition, the ICRMD 600 includes a transmitter/receiver 654 for transmitting and receiving programming instructions, parameter values, cardiac data, and other information related to the functioning of the ICRMD 600 between the medical device programmer 660. In one embodiment, transmitting and receiving of information is accomplished over a radio frequency telemetric link established between the ICRMD 600 and the medical device programmer 660.

In addition to measuring the voltage value of cardiac signals along the ST-segment, voltages values and duration of other portions of the cardiac complex can be measured using the present subject matter. For example, R-wave amplitude and duration, ST-segment duration, TQ-segment amplitude and duration, and T-wave amplitude, duration, and uniformity can be sensed and evaluated according to the present subject matter.

I claim:

1. A method, comprising:
   sensing a first cardiac electrogram signal, where the first cardiac electrogram signal has a voltage and includes a first cardiac complex;
   detecting an occurrence of a ventricular activation from the first cardiac complex;
   measuring a first voltage value of the first cardiac electrogram signal at a first specified time after the ventricular activation determined from the first cardiac complex;
   measuring a second voltage value at a defined portion of the first cardiac electrogram signal;
   calculating a comparison value from the first and second voltage values; and
   recording the first voltage value when the comparison value is greater than or equal to a predetermined value.

2. The method of claim 1, wherein measuring the second voltage value includes measuring the second voltage value between a P-wave and a Q-wave of the first cardiac complex; and
   calculating the comparison value includes subtracting the second voltage value from the first voltage value.

3. The method of claim 1, including sensing a second cardiac complex in the first cardiac signal, wherein the second cardiac complex precedes the first cardiac complex;
   calculating a ventricular activation interval from the first cardiac complex and the second cardiac complex; and
   calculating the first specified time by taking a predetermined percentage of the ventricular activation interval.

4. The method of claim 3, wherein the predetermined percentage is between approximately 2 and 50 percent of the ventricular activation interval.

5. The method of claim 1, including sensing a second cardiac complex in the first cardiac electrogram signal;
   determining an occurrence of the ventricular activation from the second cardiac complex;
   measuring the second voltage value at the first specified time after the ventricular activation determined from the second cardiac complex;
   calculating the comparison value from the first and second voltage values by calculating a rate of voltage change between the first and second voltage values.

6. The method of claim 1, including sensing a second cardiac complex in the first cardiac electrogram signal;
   detecting an occurrence of the ventricular activation from the second cardiac complex;
   measuring the first voltage value of the first cardiac electrogram signal at the first specified time after the ventricular activation determined from the second cardiac complex;

measuring the second voltage value at the defined portion of the first cardiac electrogram signal from the first cardiac complex;

measuring the second voltage value at the defined portion of the first cardiac electrogram signal from the second cardiac complex;

calculating the comparison value for the first cardiac complex from the first and second voltage values measured from the first cardiac complex;

calculating the comparison value for the second cardiac complex from the first and second voltage values measured from the second cardiac complex;

calculating a rate of voltage change between the comparison value for the first cardiac complex and the comparison value for the second cardiac complex; and recording the first voltage value of both the first cardiac complex and the second cardiac complex when the rate of voltage change is greater than or equal to the predetermined value.

7. The method of claim 1, wherein determining the occurrence of ventricular activation includes sensing a near-field electrogram signal, where a maximum deflection point of the near-field electrogram signal sensed for the cardiac complex is taken as the occurrence of the ventricular activation.

8. The method of claim 7, wherein the first specified time after the ventricular activation is a predetermined value in the range of between 20 and 500 milliseconds.

9. The method of claim 1, including starting a first timer, wherein the first timer counts off a first predetermined time; and wherein measuring the first voltage value includes measuring the first voltage value once the first predetermined time expires.

10. The method of claim 9, including starting a second timer when the comparison value is greater than or equal to the predetermined value, wherein the second timer overrides the first timer and wherein the second timer counts off a second predetermined time that has a shorter duration than the first predetermined time;

calculating the comparison value from the first and second voltage values once the second predetermined time expires; and restarting the second timer when the comparison value is greater than or equal to the predetermined value.

11. The method of claim 9, including starting a second timer when the comparison value is greater than or equal to the predetermined value, wherein the second timer counts off a second predetermined time that is of a shorter duration than the first predetermined time;

starting a duration timer, where the duration timer times an interval over which the second time period overrides the first time period; and calculating the comparison value from the first and second voltage values once the second predetermined time expires; and restarting the second timer once the second predetermined time expires for the interval of the duration timer.

12. The method of claim 1, wherein measuring the first voltage value includes acquiring two or more voltages of the first cardiac electrogram signal at a predetermined sampling frequency between the first specified time and a second specified time after the occurrence of the ventricular activation; and calculating the first voltage value from the two or more voltages.

13. The method of claim 1, including sensing a plurality of cardiac complexes in the first cardiac electrogram signal; and plotting the recorded voltage of each cardiac complex from the plurality of cardiac complexes as a function of time.

14. The method of claim 1, including positioning a first electrode in an intrathoracic space;

positioning a second electrode in a thoracic cavity; and sensing the first cardiac signal between the first electrode and the second electrode.

15. The method of claim 1, including positioning a first electrode in a coronary vein;

positioning a second electrode in a thoracic cavity; and sensing the first cardiac signal across the left ventricle between the first electrode and the second electrode.

16. The method of claim 1, including recording the first voltage value when the comparison value is less than the predetermined value.

17. An implantable cardiac rhythm management device, comprising:

a connector block having at least a first input/output socket; and control circuitry within an implantable housing, the control circuitry including:

a ventricular activation detector circuit coupled to the first input/output socket, where the ventricular activation detector circuit receives a first cardiac signal through the first input/output socket and analyzes the first cardiac signal for the occurrence of a ventricular activation in a first cardiac complex;

a cardiac morphology detector circuit coupled to the first input/output socket, wherein the cardiac morphology detector circuit is coupled to the ventricular activation detector circuit, and wherein the cardiac morphology detector circuit receives the first cardiac signal through the first input/output socket, analyzes the first cardiac signal for the occurrence of the first cardiac complex, measures a first voltage value from the first cardiac signal at a first specified time after the ventricular activation in the first cardiac complex, and measures a second voltage value of the first cardiac electrogram signal at a defined portion of the first cardiac complex;

a cardiac data processing circuit coupled to the ventricular activation detector circuit and the cardiac morphology detector circuit, wherein the cardiac data processing circuit calculates a comparison value from the first and second voltage values; and a microcontroller coupled to the cardiac data processing circuit the ventricular activation detector circuit and the cardiac morphology detector circuit, wherein a memory circuit is coupled to the microcontroller and wherein the microcontroller receives the comparison value from the cardiac data processing circuit and records the first voltage value in the memory when the comparison value is greater than or equal to a predetermined value.

18. The implantable cardiac rhythm management device of claim 17, wherein the cardiac morphology detector circuit measures the second voltage value between a P-wave and a Q-wave of the first cardiac complex.

19. The implantable cardiac rhythm management device of claim 17, wherein the ventricular activation detector circuit analyzes the first cardiac signal for the occurrence of ventricular activation in a second cardiac complex, wherein the second cardiac complex precedes the first cardiac complex;

the cardiac morphology detector circuit calculates a ventricular activation interval from the ventricular activation of the first cardiac complex and the ventricular activation of the second cardiac complex, and calculates the first specified time by taking a predetermined percentage of the ventricular activation interval.

20. The implantable cardiac rhythm management device of claim 17, wherein the ventricular activation detector circuit analyzes the first cardiac signal for the occurrence of ventricular activation in a second cardiac complex;

the cardiac morphology detector circuit analyzes the first cardiac signal for the occurrence of the second cardiac complex, measures the second voltage value from the first cardiac signal at the first specified time after the ventricular activation in the second cardiac complex; and the cardiac data processing circuit calculates the comparison value as a rate of voltage change between the first and second voltage values.

21. The implantable cardiac rhythm management device of claim 17, wherein the ventricular activation detector circuit analyzes the first cardiac signal for the occurrence of ventricular activation in a second cardiac complex;

the cardiac morphology detector circuit analyzes the first cardiac signal for the occurrence of the second cardiac complex, measures the first voltage value of the first cardiac signal at the first specified time after the ventricular activation in the second cardiac complex, measures the second voltage value at the defined portion of the first cardiac signal from the first cardiac complex, and measures the second voltage value at the defined portion of the first cardiac signal from the second cardiac complex;

the cardiac data processing circuit calculates the comparison value for the first cardiac complex from the first and second voltage values measured from the first cardiac complex, calculates the comparison value for the second cardiac complex from the first and second voltage values measured from the second cardiac complex, and calculates a rate of voltage change between the comparison value for the first cardiac complex and the comparison value for the second cardiac complex; and the microcontroller records the first voltage value of both the first cardiac complex and the second cardiac complex when the rate of voltage change is greater than or equal to the predetermined value.

22. The implantable cardiac rhythm management device of claim 17, wherein the first specified time after the ventricular activation is a predetermined value in the range of between 20 and 500 milliseconds.

23. The implantable cardiac rhythm management device of claim 17, wherein the microcontroller contains a first timer which counts off a first predetermined time, and signals the ventricular activation detector circuit and the cardiac morphology detector circuit to analyze the first cardiac signal for the occurrence of the ventricular activation in the first cardiac complex, to measure the first voltage value, and to measure the second voltage value after the first predetermined time expires.

24. The implantable cardiac rhythm management device of claim 23, wherein the microcontroller contains a second timer which overrides the first timer and counts off a second predetermined time, the second predetermined time having a shorter duration than the first predetermined time, and wherein the microcontroller starts the second timer when the comparison value is greater than or equal to the predetermined value such that the microcontroller signals the ventricular activation detector circuit and the cardiac morphology detector circuit to analyze the first cardiac signal for the occurrence of the ventricular activation in the first cardiac complex, to measure the first and second voltage values after the second predetermined time expires, and the microprocessor restarts the second timer when the comparison value is greater than or equal to a predetermined value.

25. The implantable cardiac rhythm management device of claim 23, wherein the microcontroller contains a duration timer which counts off a duration interval and a second timer which counts of a second predetermined time, where the second timer functions to override the first timer and where the second predetermined time has a shorter duration than the first predetermined time, and wherein the microcontroller starts the duration timer and the second timer when the comparison value is greater than or equal to the predetermined value such that the microcontroller signals the ventricular activation detector circuit and the cardiac morphology detector circuit to analyze the first cardiac signal for the occurrence of the ventricular activation in the first cardiac complex, to measure the first and second voltage values after the second predetermined time expires, and the microprocessor restarts the second timer once the second predetermined time expires for the interval of the duration timer.

26. The implantable cardiac rhythm management device of claim 17, where the cardiac morphology detector circuit measures two or more voltages of the first cardiac electrogram signal at a predetermined sampling frequency between the first specified time and a second specified time after the occurrence of the ventricular activation, and calculates the first voltage value of the first cardiac electrogram signal from the two or more voltages.

* * * * *

UNITED STATES PATENT AND TRADEMARK OFFICE
CERTIFICATE OF CORRECTION

PATENT NO.: 6,108,577
DATED: Aug. 22, 2000
INVENTOR(S): Benser

It is certified that error appears in the above-identified patent and that said Letters Patent is hereby corrected as shown below:

column 1, line 18, delete "ischemnia" and insert --ischemia--, therefor.

column 1, line 62, delete "measurement" and insert --measurements--, therefor.

column 2, line 22, delete "complex," and insert --complex.--, therefor.

column 8, line 32, insert --to-- after "related".

column 8, line 67, delete "take" and insert --taken--, therefor.

column 9, lines 2-3, delete the paragraph break after "described."

column 14, line 44, delete "preform" and insert --perform--, therefor.

column 15, line 48, delete "then" and insert --they--, therefor.

column 16, line 15, delete "I" and insert --we--, therefor.

column 20, line 28, delete "of" and insert --off--, therefor.

Signed and Sealed this

Tenth Day of April, 2001

Attest:

NICHOLAS P. GODICI

Attesting Officer

Acting Director of the United States Patent and Trademark Office